United States Patent [19]

Botta et al.

[11] Patent Number: 5,053,565
[45] Date of Patent: Oct. 1, 1991

[54] PROCESS FOR THE PREPARATION OF P-CHLOROTOLUENE

[75] Inventors: Artur Botta; Hans-Josef Buysch, both of Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 572,526

[22] Filed: Aug. 23, 1990

[30] Foreign Application Priority Data

Sep. 15, 1989 [DE] Fed. Rep. of Germany ....... 3930839

[51] Int. Cl.$^5$ .................. C07C 17/12; C07C 25/02
[52] U.S. Cl. ................................ 570/208; 570/206
[58] Field of Search ............................. 570/206, 208

[56] References Cited

U.S. PATENT DOCUMENTS

| 4,754,086 | 6/1988 | Higuchi et al. | 570/208 |
| 4,822,933 | 4/1989 | Suzuki et al. | 570/208 |
| 4,831,199 | 5/1989 | Suzuki et al. | 570/208 |
| 4,849,560 | 7/1989 | Sekizawa et al. | 570/208 |
| 4,914,247 | 4/1990 | Sekizawa et al. | 570/208 |

FOREIGN PATENT DOCUMENTS

| 0112722 | 7/1984 | European Pat. Off. | 570/208 |
| 2155009 | 9/1985 | European Pat. Off. | 570/208 |
| 0171265 | 2/1986 | European Pat. Off. | 570/208 |

Primary Examiner—Werren B. Lone
Attorney, Agent, or Firm—Sprung, Horn, Kramer & Woods

[57] ABSTRACT p-Chlorotoluene can be prepared in an improved manner by catalyzed reaction of toluene with a chlorinating agent if a zeolite L containing metal cations is employed as the catalyst and the reaction is carried out in the presence of methylene chloride and/or chloroform.

18 Claims, No Drawings

PROCESS FOR THE PREPARATION OF P-CHLOROTOLUENE

BACKGROUND OF THE INVENTION

The invention relates to a process for the preparation of p-chlorotoluene by chlorination of toluene in the presence of zeolite L and methylene chloride and/or chloroform.

Conventional chlorination of toluene in the presence of iron leads to a mixture of chlorotoluenes in which the o-isomer predominates over the p-isomer in a ratio of 2:1. This ratio can be shifted to values of about 1.1:1 to about 0.75:1 by cocatalysis with sulphur or sulphur compounds (European Patent Specification 292,824, U.S. Pat. No. 4,031,147 and U.S. Pat. No. 4,444,983). It is furthermore known that toluene can be converted into a chlorotoluene mixture having an o/p ratio of 1:2 in the presence of zeolite X, Y or L, without the co-use of solvents (European Patent Specification 231,662 and European Patent Specification 112,722). This ratio can be slightly improved again to about 1:3 by cocatalysis with some alcohols and/or some carboxylic acids (European Patent Specification 248,931 and European Patent Specification 154,236).

For the majority of industrial uses, p-chlorotoluene is the more useful product; it was therefore desirable for the preparation processes disclosed to date to be improved further in respect of p-selectivity.

SUMMARY OF THE INVENTION

A process has been found for the preparation of p-chlorotoluene by catalyzed reaction of toluene with a chlorinating agent, which is characterized in that a zeolite L containing metal cations is employed as the catalyst and the reaction is carried out in the presence of methylene chloride and/or chloroform.

DETAILED DESCRIPTION OF THE INVENTION

The o-/p-isomer ratio of the chlorotoluenes can be shifted into ranges of 1:4 and even 1:5.5 with the aid of the process according to the invention. This finding is exceptionally surprising, since it was not to be expected that the co-use of methylene chloride and/or chloroform, which are usually considered only as diluents, could have any influence at all on the o-/p-isomer ratio. This finding is furthermore surprising since comparable solvents, such as carbon tetrachloride, 1,1,1-trichloroethane or 1,2-dichloropropane, do not have the effect of such a further shift in the isomer ratio.

The further shift in the isomer ratio in the context of the process according to the invention represents a considerable improvement in the profitability in the case of a large-scale product such as p-chlorotoluene.

Possible chlorinating agents in the process according to the invention are chlorine and substances which liberate chlorine, such as sulphuryl chloride, N-chloroamines or N-chloroamides. Elemental chlorine is preferably employed. The halogenating agent is as a rule employed in a stoichiometric ratio with the toluene, that is to say in a molar ratio of about 1:1. The ratio can deviate from this stoichiometric ratio upwards by up to 50, preferably up to 30% or downwards by up to 60%, preferably up to 40%, in order to influence the degree of reaction and/or the p-selectivity, according to the existing need, in a manner known to the expert.

The process according to the invention is carried out in the presence of zeolite L as a catalyst, at least some of all the replaceable cations in this catalyst being metal cations.

Zeolites are crystalline alumosilicates which are built up from a network of $SiO_4$ and $AlO_4$ tetrahedra. The individual tetrahedra are linked to one another at the corners by oxygen bridges and form a spatial network through which channels and hollow spaces run. Replaceable cations are intercalated to compensate for the negative charge of the framework. At least some of the Si and Al in the zeolites can be replaced by other elements. A detailed description of zeolites is given, for example, in the monograph by D. W. Breck "Zeolite Molecular Sieves, Structure, Chemistry and Use", J. Wiley and Sons, N.Y., 1974.

The zeolites of the L type which are suitable for the process according to the invention have pore widths of about 7 Å and an Si:Al ratio of 2.6–3.5:1. Such zeolites are known in principle to the expert.

A zeolite L in which 60–100 equivalent %, preferably 80–100 equivalent % and particularly preferably 90–100 equivalent % of all the cations are metal cations is suitable for the use according to the invention. Examples of possible such metal cations are: cations of the alkali metals Li, Na, K, Rb and Cs, the ammonium cation, the cations of the alkaline earth metals, such as Ca, Mg, Sr and Ba, the cations of the rare earth metals, such as La and Ce, and the cations of other metals, such as Cu, Fe, Zn, Mn, Cr, Co, Ni, Ti, Ag and Pb. Mixtures of such cations of course also be present. The cations of the metals K, Rb, Cs, Ca, Sr, Ba, Ag or Pb or mixtures of these are preferably present. Cations of the metals K, Rb, Ca, Sr, Ba, Pb or Ag or mixtures of these are particularly preferably present.

The zeolite catalyst is employed in an amount of 1–100% by weight, preferably 3–50% by weight, particularly preferably 5–30% by weight, based on the weight of the toluene.

The shape of the employed zeolite catalyst is not critical for the process according to the invention, in general. As a rule, especially in a batch variant, the catalyst can be used as a powder. Of course, it is also possible (e.g. in a continuous reaction in the gas, liquid or trickle phase, wherein the catalyst is arranged as a fixed bed) to use the catalyst in pieces or in granulated form to yield a better separation from the reaction product. Herewith usual binding and forming auxiliary agents which are known to the killed artisan may be co-used which are inert towards the halogenating agents, e.g. $SiO_2$, $Al_2O_3$, argillaceous earth, graphite etc. in an amount of 0.1–80%, preferably 2–30% by weight, relative to the amount of the pure zeolite.

The process according to the invention is furthermore characterized by the co-use of methylene chloride and/or chloroform. Methylene chloride and/or chloroform are employed here in 0.05–100 times, preferably in 0.2–50 times and particularly preferably in 0.5–10 times the amount by weight of toluene. Methylene chloride or a mixture containing at least 50% by weight, preferably at least 70% by weight and particularly preferably at least 90% by weight of methylene chloride is preferably employed as the diluent.

The diluents which can be used in addition to the methylene chloride and/or chloroform are, for example, those which are inert towards the chlorinating agents, for example hydrocarbons or halogenohydrocarbons, such as petroleum ether, carbon tetrachloride, 1,1,1-trichloroethane, 1,2-dichloroethane, 1,2-dichloropropane, perchloroethane, perchloroethylene, lower carboxylic acids, such as acetic acid, and other diluents known to the expert. However, since such diluents which can be co-used produce no additional effect, the sole use of methylene chloride and/or chloroform, preferably of methylene chloride, is preferred, in favour of easier working up.

It is furthermore acceptable for co-catalysts known to the expert, such as lower alcohols, lower carboxylic acids, sulphur compounds and/or quaternary ammonium salts, to be used in the process according to the invention. The process is preferably carried out without such co-catalysts.

The process according to the invention is carried out at a temperature of −20° C. to +120° C., preferably 0°–90° C. and particularly preferably 10°–70° C. The pressure is not critical for the course of the process according to the invention and is only of importance, for example, for keeping the majority of the methylene chloride in the liquid phase of the reaction mixture at elevated temperature. In this procedure, the reaction is preferably carried out under the intrinsic pressure established in the reaction mixture. A reduced pressure could be important if the reaction is to be carried out at a temperature below the boiling point of the diluent under reflux conditions, for control of the reaction temperature (vapour cooling). These relationships are known to the expert. In all cases where the procedure under normal pressure is possible, such a procedure is preferred.

In carrying out the process according to the invention in a discontinuous procedure, for example, the toluene can be mixed with the diluent (if appropriate with addition of one of the co-catalysts mentioned), after which the zeolite catalyst is added in powder form or in form of granulated pieces. The chlorinating agent is then passed into the liquid-disperse phase at the reaction temperature at the rate at which it is consumed, while stirring.

Column apparatuses, for example, in which the zeolite catalyst is arranged in the form of granulated pieces or in powder form on various trays are suitable for the continuous procedure. The toluene-methylene chloride mixture and the chlorinating agent are passed over such an arrangement either in co-current or in counter-current.

The p-chlorotoluene is as a rule isolated and purified, often after removal of the catalyst, by distillation under normal or reduced pressure.

The zeolite catalyst which remains either as the distillation residue or as the filtration residue can in general be used again according to the invention several times without further activation. If a reduction in activity is observed after the zeolite catalyst has been re-used several times it can be reactivated by a customary process, for example by calcining at elevated temperature (about 400°–600° C.).

EXAMPLES

All the zeolites mentioned in the following examples were activated in a muffle furnace at 400° C. for 2–3 hours before being used.

EXAMPLE 1-7

35.5 g (0.5 mol) of chlorine were passed, at 40° C. in the course of 5 hours and while stirring, into a suspension of 9.2 g (20% strength, based on toluene) of K zeolite L in powder form, 46 g of toluene (0.5 mol) and X g of $CH_2Cl_2$ in a three-necked stirred apparatus made of glass (round-bottomed flask). The mixture was then subsequently stirred for a further 15 minutes, while passing through nitrogen. The results of analysis by gas chromatography can be seen from Table 1 (data in all the tables in area %).

EXAMPLES 8-11

In the same procedure as in Example 6, the amount of catalyst K-L was varied from 5 to 25% by weight. The results of the analysis by gas chromatography can be seen from Table 2.

EXAMPLES 12-15 (COMPARISON EXAMPLES)

In the same procedure as in Examples 1-7, the nature of the catalyst was varied, using 50 ml of methylene chloride and a reaction temperature of 40° C. Further details and the results of the analysis of the composition of the reaction mixture by gas chromatography are summarized in Table 3.

TABLE 1

| Example | X g of $CH_2Cl_2$ | Toluene | Chlorotoluene 2- | Chlorotoluene 4- | Benzyl chloride | Dichlorotoluene 2,4- | Dichlorotoluene 3,4- | Remainder | 4-Selectivity |
|---|---|---|---|---|---|---|---|---|---|
| 1 | 2.3 | 10.5 | 28.5 | 58.6 | 0.6 | 0.6 | 0.2 | 0.9 | 65 |
| 2 | 4.6 | 5.9 | 31.6 | 59.1 | 1.7 | 0.7 | 0.2 | 0.9 | 63 |
| 3 | 9.2 | 6.5 | 27.3 | 64.1 | 0.6 | 0.6 | 0.2 | 0.7 | 69 |
| 4 | 23 | 6.1 | 22.2 | 69.0 | 0.6 | 0.8 | 0.2 | 1.3 | 73 |
| 5 | 46 | 11.5 | 17.4 | 70.3 | 0.2 | 0.3 | — | 0.4 | 79 |
| 6 | 69 | 10.8 | 15.6 | 72.6 | 0.2 | 0.3 | 0.2 | 0.3 | 81.4 |
| 7 | 138 | 8.7 | 14.9 | 75.6 | 0.4 | 0.3 | — | 0.1 | 83 |

TABLE 2

| Example | % by weight of catalyst | Toluene | Chlorotoluene 2- | Chlorotoluene 4- | Benzyl chloride | Dichlorotoluene 2,4- | Dichlorotoluene 3,4- | Remainder | 4-Selectivity |
|---|---|---|---|---|---|---|---|---|---|
| 8 | 5 | 12.7 | 16.9 | 68.3 | 0.9 | 0.4 | 0.09 | 0.7 | 78 |
| 9 | 10 | 7.8 | 17.2 | 73.7 | 0.5 | 0.4 | 0.09 | 0.3 | 80 |
| 10 | 15 | 5.4 | 17.3 | 75.6 | 0.7 | 0.5 | 0.08 | 0.4 | 80 |
| 6 | 20 | 10.8 | 15.6 | 72.6 | 0.2 | 0.3 | 0.2 | 0.3 | 81.4 |
| 11 | 25 | 9.1 | 16.8 | 73.4 | 0.2 | 0.3 | — | 0.2 | 81 |

TABLE 3

| Example | Catalyst | Toluene | Chlorotoluene 2- | Chlorotoluene 4- | Benzyl chloride | Dichlorotoluene 2,4- | Dichlorotoluene 3,4- | Remainder | 4-Selectivity |
| --- | --- | --- | --- | --- | --- | --- | --- | --- | --- |
| 12 | none | 27.60 | 0.67 | 0.41 | 62.37 | 5.54 | — | 3.41 | 0.6% |
| 13 | 1% of FeCl$_3$ | 21.86 | 46.76 | 18.26 | — | 6.74 | 2.05 | 4.33 | 23.4% |
| 14 | H-Mordenite | 14.76 | 54.18 | 26.39 | — | 1.62 | 0.34 | 2.71 | 31.0% |
| 15 | H-ZSM-5 | 29.1 | 11.51 | 6.02 | 41.75 | 0.16 | 0.03 | 11.43 | 8.5% |
| 16 | Rb-L | 15.54 | 15.05 | 67.64 | 0.58 | 0.37 | 0.08 | 0.74 | 80.1% |
| 17 | Ag-L | 27.44 | 13.10 | 58.13 | 0.41 | 0.19 | 0.05 | 0.68 | 80.1% |
| 18 | Pb-L | 7.35 | 18.47 | 72.32 | 0.46 | 0.42 | 0.08 | 0.90 | 78.1% |

EXAMPLES 16–18

The procedure was analogous to Examples 1–7, the metal cations of the zeolite L being varied, at a reaction temperature of 40° C. and using 50 ml of methylene chloride. Further details and the results of the analyses by gas chromatography can likewise be seen from Table 3.

EXAMPLES 19–24

The chlorination reaction on toluene was carried out analogously to Examples 1–7 with K–L as the catalyst, a reaction temperature of 20° C. and 50 ml of various solvents. The nature of the solvent and further details as well as the findings on the composition of the reaction mixtures by analysis by gas chromatography are summarized in Table 4.

EXAMPLES 25–30

In the same procedure as in Example 6, the toluene chlorination was carried out at a reaction temperature of 40° C. in 69 g of a mixture of methylene chloride and chloroform. The details of the mixing ratio and the results of the analysis of the reaction mixtures by gas chromatography can be seen from Table 5.

EXAMPLE 31

368 g (4 mol) of toluene and 1,104 g of methylene chloride were brought together in a glass reactor with a ground glass flange (height 25 cm, diameter 9 cm) fitted with a stirrer, thermometer, reflux condenser and a gas inlet tube extending to the bottom, and 73.6 g of pulverulent K zeolite L were added. A total of 312 g (4.4 mol) of Cl$_2$ gas were passed into the suspension at 40° C. in the course of 10 hours, while stirring. After 90% (255.6 g), 100% (284 g) and 110% (312 g) of the theoretically required amount of Cl$_2$ had been passed in, samples were taken to determine the conversion. The results of the analysis of the product composition by gas chromatography can be seen from Table 6.

EXAMPLE 32

According to the method of example 31 in a glass reactor with a ground glass flange (height 11 cm; diameter 5.5 cm) 55.3 g (0.6 mole) toluene in 120 ml methylene chloride were reacted with Cl$_2$ at 40° C. within 6 hours in the presence of 13.0 g of K-zeolite L-granulate (bound with 15% SiO$_2$). Samples for the gaschromatographic test were taken when 90% (38.3 g) or else 100% (42.6 g) or else 110% (46.9 g) of Cl$_2$ had been passed in.

EXAMPLE 33

The performance was in analogy to example 31 using 15.8 g K/Na-zeolite L (granulate bound with 30% Al$_2$O$_3$).

The result of examples 32 and 33 are summarized in table 7.

TABLE 4

| Example | Solvent | Toluene | Chlorotoluene 2- | Chlorotoluene 4- | Benzyl chloride | Dichlorotoluene 2,4- | Dichlorotoluene 3,4- | Remainder | 4-Selectivity |
| --- | --- | --- | --- | --- | --- | --- | --- | --- | --- |
| 19 | Cyclohexane | 12.66 | 32.02 | 53.07 | — | 0.53 | 0.12 | 1.60 | 60.8 |
| 20 | n-Hexane | 66.20 | 12.26 | 19.18 | 0.20 | 0.25 | 0.08 | 1.83 | 56.7 |
| 21 | 1,2-Dichloropropane | 16.45 | 20.47 | 54.28 | 1.18 | 0.94 | — | 6.68 | 64.9 |
| 22 | 1,1,1-Trichloroethane | 44.29 | 14.70 | 19.91 | 9.53 | 0.21 | 0.11 | 11.25 | 35.7 |
| 23 | CHCl$_3$ | 40.80 | 14.70 | 43.57 | — | 0.42 | 0.06 | 0.45 | 73.0 |
| 24 | CCl$_4$ | 8.49 | 33.83 | 55.90 | — | 0.72 | 0.18 | 0.88 | 61.1 |

TABLE 5

| Example | % by weight of CHCl$_3$ in CH$_2$Cl$_2$ | Toluene | Chlorotoluene 2- | Chlorotoluene 4- | Benzyl chloride | Dichlorotoluene 2,4- | Dichlorotoluene 3,4- | Remainder | 4-Selectivity |
| --- | --- | --- | --- | --- | --- | --- | --- | --- | --- |
| 25 | 100 | 9.24 | 23.39 | 64.74 | 0.47 | 0.56 | 0.13 | 1.47 | 71.3 |
| 26 | 50 | 5.33 | 19.57 | 70.51 | 1.95 | 0.46 | 0.07 | 2.11 | 74.5 |
| 27 | 25 | 9.34 | 17.32 | 70.28 | 0.68 | 0.47 | 0.15 | 1.76 | 77.5 |
| 28 | 10 | 14.06 | 15.91 | 66.05 | 1.09 | 0.36 | 0.12 | 2.41 | 76.9 |
| 29 | 5 | 16.47 | 15.72 | 66.57 | 0.30 | 0.33 | 0.06 | 0.55 | 79.7 |
| 30 | 2 | 9.56 | 16.74 | 72.04 | 0.15 | 0.30 | — | 1.21 | 79.7 |
| 6 | 0 | 10.8 | 15.6 | 72.6 | 0.20 | 0.3 | 0.2 | 0.30 | 81.4 |

TABLE 6

| Example | Sample at | Toluene | Chlorotoluene 2- | Chlorotoluene 4- | Benzyl chloride | Dichlorotoluene 2,4- | Dichlorotoluene 3,4- | Remainder | 4-Selectivity |
| --- | --- | --- | --- | --- | --- | --- | --- | --- | --- |
| 31 | 90% of Cl$_2$ | 21.61 | 12.41 | 65.41 | 0.24 | 0.13 | — | 0.20 | 83.4 |

TABLE 6-continued

| Example | Sample at | Toluene | Chlorotoluene 2- | Chlorotoluene 4- | Benzyl chloride | Dichlorotoluene 2,4- | Dichlorotoluene 3,4- | Remainder | 4-Selectivity |
|---|---|---|---|---|---|---|---|---|---|
| | 100% of Cl$_2$ | 11.83 | 13.99 | 73.53 | 0.30 | 0.20 | — | 0.15 | 83.4 |
| | 110% of Cl$_2$ | 1.94 | 15.42 | 81.61 | 0.35 | 0.43 | 0.05 | 0.20 | 83.2 |

TABLE 7

| Example | Sample at % Cl$_2$ | Toluene | Chloro- toluene 2- | Chloro- toluene 4- | Benzyl- chloride | Dichloro- toluene 2,4- | Dichloro- toluene 3,4- | Remainder | 4-Selectivity % |
|---|---|---|---|---|---|---|---|---|---|
| 32 | 90 | 14.0 | 16.4 | 67.5 | 0.6 | 0.2 | 0.1 | 1.2 | 79.8 |
| | 100 | 4.5 | 18.2 | 74.6 | 0.7 | 0.2 | 0.3 | 1.5 | 79.9 |
| | 110 | — | 17.0 | 76.0 | 0.6 | 1.2 | 1.9 | 3.3 | 81.4 |
| 33 | 90 | 19.0 | 20.6 | 58.7 | 0.4 | 0.1 | 0.2 | 1.0 | 73.4 |
| | 100 | 10.4 | 23.0 | 64.3 | 0.4 | 0.2 | 0.3 | 1.4 | 73.0 |
| | 110 | 0.9 | 25.3 | 70.0 | 0.4 | 0.6 | 0.8 | 2.0 | 70.1 |

What is claimed is:

1. A process for the preparation of p-chlorotoluene by catalyzed reaction of toluene with a chlorinating agent selected from the group consisting of chlorine and substances which liberate chlorine, including sulphuryl chloride, N-chloroamines and N-chloroamides, wherein a zeolite L containing metal cations is employed as the catalyst and the reaction is carried out in the presence of methylene chloride and/or chloroform, at a reaction temperature of from about −20° C. to +120° C.

2. The process of claim 1, wherein the catalyst is employed in an amount of 1–100% by weight, based on the weight of the toluene.

3. The process of claim 2, wherein the catalyst is employed in an amount of 3–50% by weight, based on the weight of the toluene.

4. The process of claim 1, wherein the catalyst is employed in an amount of 5–30% by weight, based on the weight of the toluene.

5. The process of claim 1, wherein 60–100 equivalent % of all the cations in zeolite L are metal cations.

6. The process of claim 5, wherein 80–100 equivalent % of all the cations in zeolite L are metal cations.

7. The process of claim 6, wherein 90–100 equivalent % of all the cations in zeolite L are metal cations.

8. The process of claim 1, wherein the metal cations employed are those of the alkali metals, the alkaline earth metals, rare earth metals, copper, iron, zinc, manganeses, chromium, cobalt, nickel, titanium, silver or lead or a mixture of these.

9. The process of claim 8, wherein the metal cations employed are those of K, Rb, Cs, Ca, Sr, Ba, Ag or Pb or mixtures of these.

10. The process of claim 9, wherein the metal cations employed are those of K, Rb, Ca, Sr, Ba, Pb or Ag or mixtures of these.

11. The process of claim 1, wherein methylene chloride and/or chloroform is employed in 0.05–100 times the amount by weight of toluene.

12. The process of claim 11, wherein methylene chloride and/or chloroform is employed in 0.2–50 times the amount by weight of toluene.

13. The process of claim 12, wherein methylene chloride and/or chloroform is employed in 0.5–10 times the amount by weight of toluene.

14. The process of claim 1, wherein the reaction is carried out at a temperature in the range from 0°–90° C.

15. The process of claim 14, wherein the reaction is carried out at a temperature in the range of 10°–70° C.

16. The process of claim 1, wherein the reaction is carried out in the presence of methylene chloride or a mixture containing at least 50% by weight of methylene chloride, as the diluent.

17. The process of claim 16, wherein the reaction is carried out in the presence of methylene chloride or a mixture containing at least 70% by weight of methylene chloride, as the diluent.

18. The process of claim 17, wherein the reaction is carried out in the presence of methylene chloride or a mixture containing at least 90% by weight of methylene chloride, as the diluent.

* * * * *

UNITED STATES PATENT AND TRADEMARK OFFICE
CERTIFICATE OF CORRECTION

PATENT NO. : 5,053,565

DATED : October 1, 1991

INVENTOR(S) : Botta et al.

It is certified that error appears in the above-identified patent and that said Letters Patent is hereby corrected as shown below:

Col. 7, line 37    Delete " claim 1 " and substitute -- claim 3 --

Signed and Sealed this

Eighteenth Day of May, 1993

Attest:

MICHAEL K. KIRK

*Attesting Officer*    *Acting Commissioner of Patents and Trademarks*